(12) United States Patent
Goldberg et al.

(10) Patent No.: US 6,245,294 B1
(45) Date of Patent: Jun. 12, 2001

(54) METHOD AND APPARATUS FOR SURFACE TREATMENT OF MATERIALS

(75) Inventors: Neil M. Goldberg, North Wales; E. Richard Radewonuk, Woodlyn; Michael F. Kozempel, Hatfield, all of PA (US); Arthur I. Morgan, Berkeley, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/213,804

(22) Filed: Dec. 17, 1998

(51) Int. Cl.[7] ....................................................... A61L 2/08
(52) U.S. Cl. .................. 422/26; 99/472; 99/516; 422/28; 422/32; 422/292; 422/297; 426/312; 426/511
(58) Field of Search ................. 422/28, 26, 33, 422/292, 297; 426/236, 320, 335, 312, 511; 99/472, 516

(56) References Cited

U.S. PATENT DOCUMENTS

| | | | |
|---|---|---|---|
| 4,952,370 | * 8/1990 | Cummings et al. | 422/28 |
| 5,281,428 | * 1/1994 | Morgan | 426/312 |
| 5,961,922 | * 10/1999 | Witte et al. | 422/33 |
| 6,066,348 | * 5/2000 | Yuan et al. | 426/236 |

* cited by examiner

*Primary Examiner*—Krisanne Thornton
(74) *Attorney, Agent, or Firm*—M. Howard Silverstein; Joseph A. Lipovsky; John D. Fado

(57) ABSTRACT

The killing of microorganisms on the surface of porous and non-porous materials including agricultural commodities is accomplished by use of methods and apparatus which expose the material to controlled applications of a biocidal treatment gas into a sub-atmospheric environment. The material is first exposed to a vacuum then, without an intervening flush step, full treated with an air-free treatment gas prior to being re-exposed to a vacuum. The method and apparatus successfully kill microorganisms both on the surface and within the pores or structural recesses of the material without causing significant deleterious changes to the material.

15 Claims, 9 Drawing Sheets

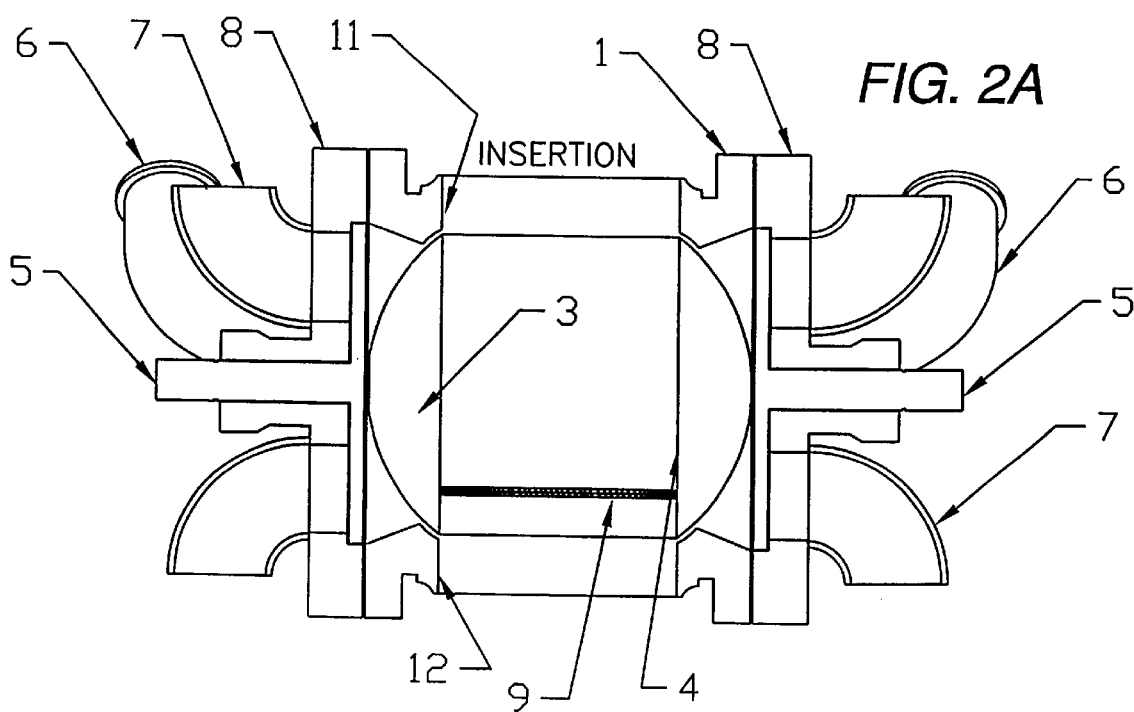

CLOSED

VACUUM

TREATMENT

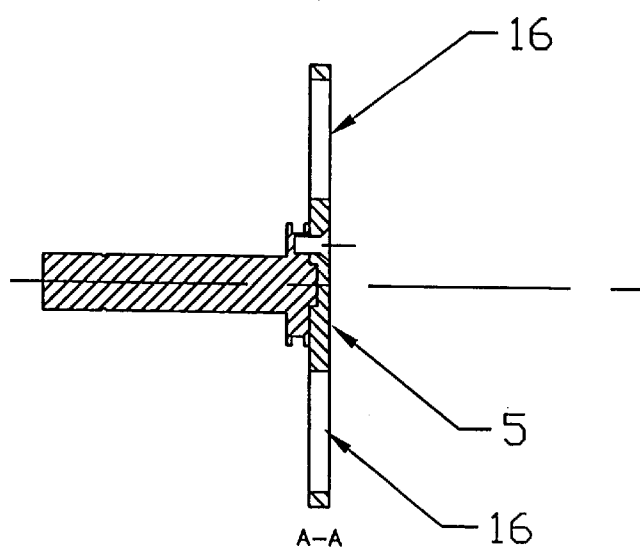
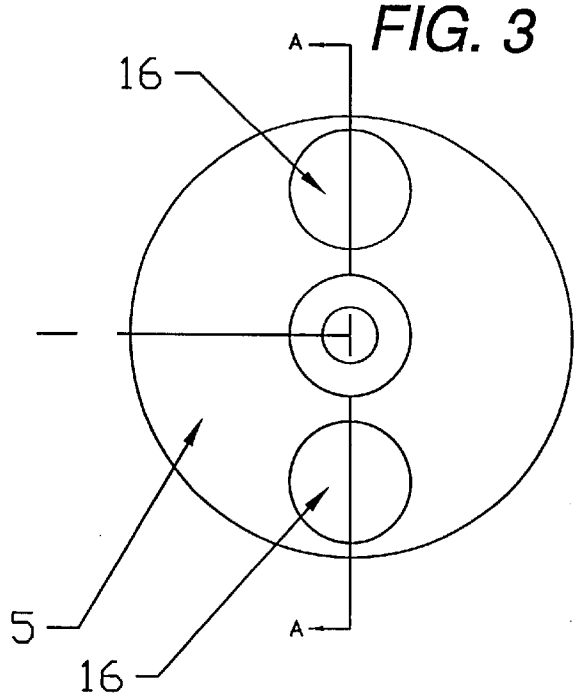
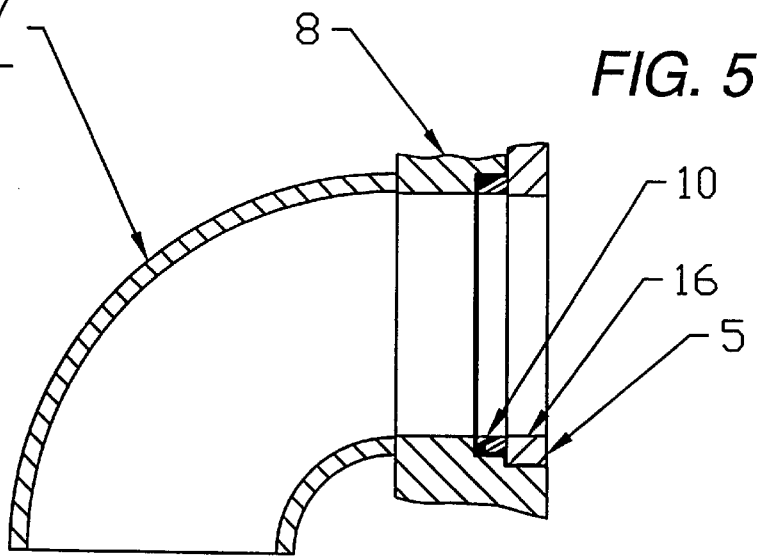

METHOD AND APPARATUS FOR SURFACE TREATMENT OF MATERIALS

BACKGROUND OF THE INVENTION

1. Field of the Invention

The present invention relates generally to processes and apparatuses for the pasteurization of materials, and more particularly to a method and device for killing microorganisms on food materials such as raw meat, fruits and vegetables through controlled application of a biocidal treatment gas into a subatmospheric environment.

2. Description of the Prior Art

Prior to slaughter, the muscles of healthy food animals normally do not contain microorganisms toxic to humans. The animal's gastrointestinal tract, will however harbor several species of microorganisms. Typically, the host of gastrointestinal microorganisms found in animals will include numerous species of bacteria. Enterobacteria such as Salmonella is especially prevalent. While these microorganisms are generally not harmful to the animal, several species will produce toxic reactions in humans.

Unfortunately, an essential part of slaughter is the cutting and removal of an animal's gastrointestinal tract. Not surprisingly, the tract's contents are often spilled and smeared onto the meat surface during and after slaughter. Further contributing to bacterial contamination, gastrointestinal tract contents are often spread from the surface of one animal to another as the result of successive handling by slaughterhouse workers. Contamination can also occur during successive machine-processing steps and when meat pieces are sequentially dipped in various liquid treatment baths. Generally, surface-to-surface contamination can occur throughout every stage in any standard meat slaughtering, processing and packaging assembly-line.

As pointed out in Busch et al. (U.S. Pat No. 3,934,044) many techniques have been employed in the past for treating meat and meat cuts in order to destroy surface bacterial flora. As noted by Busch et al. however, all of these techniques have suffered from one or more of the following problems: (1) denaturation of meat protein, (2) insufficient bacterial kill, (3) deleterious color change, (4) unacceptable flavor modification, and (5) inadequate control of the process in large scale operations.

The problems enumerated by Busch et al. are evident in several other previous and subsequent patents. For example, Malkki et al. (U.S. Pat. No. 3,996,386) attempts to prevent microbial surface deterioration of foods by spraying the surface of such foods with a preservative in the form of a fine particulate aerosol. Suggested preservatives include chlortetracycline, chloramphenicol, sodium o-phenyl phenolate and others. While this process provides a means for countering surface bacterial growth it still results in a chemically coated food substance despite efforts to minimize actual amounts of preservatives used. Accordingly, potential exists for chemical interactions leading to undesirable color change and/or flavor modification.

In the same vein, Robinson et al. (U.S. Pat. No. 4,636,395) describes a method for heat treating the surface area of raw meats by rapidly elevating the temperature of the meat followed immediately by rapid cooling. Although Robinson et al. does not use taste and/or color modifying preservatives, their process is delicately balanced between the competing objectives of maximizing sufficient bacterial kill and preventing the denaturation of meat protein. It is believed that this balance struck by Robinson et al. is one that can be consistently maintained only with difficulty and constant vigilance due to its having very few safeguards. In actual practice of the Robinson et al. technology one objective will often have to give way to the other.

The Busch et al. process (U.S. Pat. No. 3,934,044) attempts to correct the several noted problems. Busch et al. describes a process directed at destroying psychotropic spoilage bacteria on meat or meat-cuts without adversely affecting the color, flavor or aroma of the meat by applying a hot, dilute acid solution to meat surfaces for a brief period of time. However, in the attempt to correct the inherent problems associated with the pasteurization of meat products, Busch et al. overlooks the problem of surface irregularities, that were identified by Malkki et al. in their later patent.

These irregularities, in the form of pores and other imperfections found on the surface of meat, will often serve as fertile grounds for the development of bacterial growth. The removal of surface contamination from meat through use of conventional pasteurization procedures has been further frustrated by the strong adhesion of microorganisms to the meat surface. When a wash or spray is used, many organisms tend to escape. While better results were achieved with the addition of bactericides to the spray or wash water, the improvement was slight. Even with the use of concentrated and powerful significant number of organisms still often survived. This occurred even when the exposure time and bactericide concentration were more than adequate to sterilize, a smooth, simple surface.

In accordance with the invention of Morgan (U.S. Pat. No. 5,281,428, hereby incorporated by reference) the failure of prior processes could be ascribed to chemical and physical attributes of the solvent, water. Generally, water cannot reach deep contaminated surfaces because of its high surface tension. Many other solvents used for microbial kill exhibit similarly high surface tension. The folds, cavities and pores are often large enough to contain bacteria; but too small to admit a liquid wash or spray—with this resulting in the need for use of an impractically high wash pressure to overcome the capillary pressure in pores having dimensions just large enough to contain bacteria.

Many species of microorganisms are small relative to the surface irregularities in which they live. Many parts of the muscles are about the same size as the typical target organism, $2 \times 10^{-6}$ m. Poultry muscle fibers, for example, are about $20 \times 10^{-6}$ m. in diameter; and these each consist of three distinct sheaths, covering many of the much finer fibrils. These fibrils are generally of two kinds: thick and thin. The thick fibrils are $0.1 \times 10^{-6}$ m. wide and $2 \times 10^{-6}$ m. long. The thin fibrils are $0.05 \times 10^{-6}$ m. wide and $0.4 \times 10^{-6}$ m. long. In addition, there are several other structures, such as Z discs, mitochondria, capillaries, and cell nuclei in the muscles, capable of obscuring the targets. Furthermore, certain toxic bacteria, such as Salmonella, have short flagella on their surface which may entangle with the meat fibers or fibrils. In view of this, one can appreciate the difficulties inherent in cleaning meat products.

With these issues in mind, Morgan developed and patented an apparatus and process involving a requisite 4-step treatment for the killing of the microorganisms on porously surfaced materials such as meat. These steps require the sequential use of a first vacuum, a flush, a gas treatment and a second vacuum.

It is in light of the precedent invention of Morgan, that the present invention was designed. In the most general sense, the present invention provides a means to kill microorganisms on both porous and non-porous material surfaces without damaging the material itself and without need for a flushing step—thus increasing the effective speed of treatment. None of the patents discussed above, taken either singly or in combination, describe or suggest the instant invention as claimed.

SUMMARY OF THE INVENTION

This invention relates to the processing of porous and non-porous materials to reduce the number of toxic microorganisms living on the surface and within the surface recesses or pores of such material. The process involves the highly controlled exposure of the material to a biocidal treatment gas such as steam, capable of killing microorganisms without leaving a toxic residue or producing any other undesired changes in the quality of the material.

It is noted that the present invention kills the target organisms in situ and does not remove them. Dead enterobacteria are generally not harmful to humans as they neither form spores nor produce any toxins which act after their death.

In view of the above, it is an object and purpose of the instant invention to reduce counts of organisms residing on the surface and surface recesses of a wide variety of porous and non-porous materials.

Another object of the instant invention is to provide a means of reducing organism counts on non-food materials such as clothing, surgical equipment, storage containers and filter equipment so as to reduce the potential for their infectivity.

It is a further object to convert food products contaminated with microorganisms into surface treated materials with reduced capacity of causing disease or contamination of other foods during distribution, sale, storage, preparation or consumption.

It is a specific object of this invention to convert meat contaminated with gastrointestinal organisms during the slaughter and subsequent processing into surface treated meat with reduced capacity of causing disease or contamination.

It is a further object of the present invention to provide a food treatment process which avoids making noticeable changes to the interior of the food material.

Yet another object of the present invention is to provide a process that may be used to treat uniformly any surface with a gas in such a way that it is begun and ended so abruptly as to have no appreciable effect on the solid below the treated surface.

It is a further object to kill microorganisms in situ without their physical removal.

With these and other objects, the nature of which will be more readily ascertained upon review of the succeeding description and examples, the invention consists of the novel construction, combination and assembly of parts hereinafter more fully described, illustrated and claimed with reference being made to the attached drawings.

BRIEF DESCRIPTION OF THE DRAWINGS

FIG. 1 is a flow chart outlining the basic steps involved in the treatment process.

FIGS. 2A, 2B and 2C are schematic representations of a preferred material treating apparatus product valve at various stages throughout the material treating process.

FIG. 3 is an end view of the treatment valve rotor of the preferred material treating apparatus.

FIG. 4 is a lateral section of the treatment valve of the preferred material treating apparatus.

FIG. 5 is a sectional detail of the seal mechanism joining the treatment valve rotor and the headplate of the treatment valve of the preferred material treating apparatus.

DETAILED DESCRIPTION OF THE INVENTION

I. The Process

Figure 2B:
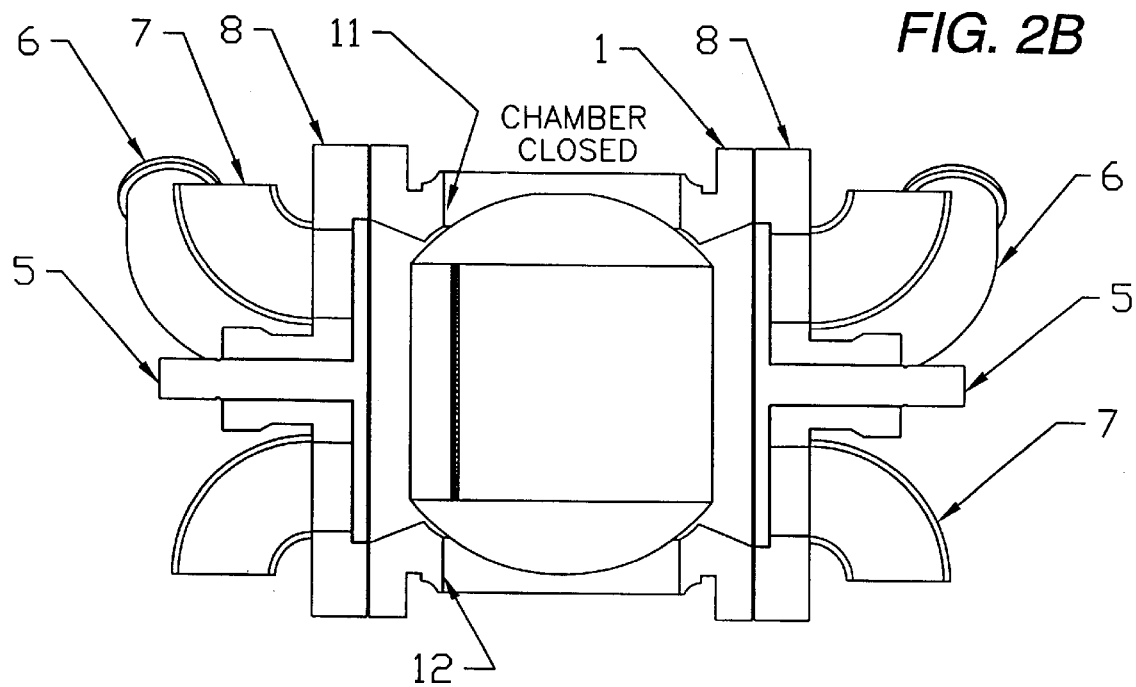

FIG. 1 provides a basic flow chart which generally outlines the five basic steps in killing microorganisms on the surface of materials. As shown in FIG. 1, the first step involves isolating the materials from the environment. The second step involves exposing the materials to a vacuum. The third step involves treating the materials with the treatment gas. The fourth step involves again exposing the materials to a vacuum. The fifth step involves opening the product chamber and returning the materials to the environment.

In accordance with this invention, the treating substance applied is selected from one or more gases, such as steam, ozone, chlorine dioxide, hydrogen peroxide, ethylene oxide, methyl bromide, chlorine, iodine, bromine and formaldehyde; with steam being preferred. The treatment gases are applied in a substantially air-free form, herein defined as being greater than 80% on a volume/volume basis. Use of such gases avoids the difficulties concerning penetration into surface irregularities such as pores and recesses, that otherwise might have the capacity of reducing microbial kill. Due to their small size, these gases can enter any cavity large enough to contain microorganisms such as bacteria. Other gases possessing similar properties may be used. To illustrate this point, it is noted that Salmonellae are short straight rods about $0.7 \times 10^{-6}$ m in thickness and $4 \times 10^{-6}$ m long. Simple gas molecules are typically $2 \times 10^{-10}$ m in diameter and are hence 10,000 times smaller than a bacterium. Gas condensation velocity is appreciably reduced only in cavities whose diameter is shorter than the mean free path of the gas. As a preferred condition for this invention, the mean free path of the gas should not exceed about $0.3 \times 10^{-6}$ m during treatment. This is about half the diameter of a cavity capable of containing a Salmonella. From this it can be anticipated that the treatment gases can quickly reach all toxic surface microorganisms.

The vapor pressure within small wetted cavities is reduced by surface tension, however this effect is negligible for cavities large enough to contain a pathogenic bacterium such as salmonella. Although ordinary steam may reach and kill all surface bacteria, such may not be accomplished prior to the material having received a dose of heat sufficient to cause irreversible changes associated with the cooking process. To accomplish surface treatment with minimal interior involvement, the gas must reach the surface very rapidly. Gas approaches a surface by means of either streaming or diffusion. Streaming is motivated by pressure gradient and is very rapid. Diffusion is motivated by the concentration gradient of the treating gas passing through other gases, and is much slower.

It was previously hypothesized by Morgan in U.S. Pat. No. 5,281,428 that during gas treatment, air or any other non-condensable gas present would concentrate near the material surface as the result of being pushed there by the rush of incoming treatment gas. This air was believed to form a boundary layer of non-condensable gas near the material surface to be treated and thus impede the rate of material transfer of the treatment gas due to the requirement that such action be done by diffusion. This would, in turn, markedly increase the time for microbial kill. Due to this supposition, Morgan considered it requisite that, subsequent to an initial exposure to vacuum, it was necessary to flush the chamber with air-free gas. It has now been found with the instant invention that utilization of a flushing step is not necessary for the effective operation of this process.

While either superheated or supersaturated steam is useable for treatment with the apparatus and process of the instant invention, for optimization of thermal efficiency and minimization of processing time it is preferred that steam be used as close to its saturation temperature as practicable. This is because superheated steam is capable of condensation only after first cooling to saturation temperature, with this initial cooling step being thermally inefficient as compared to the process of condensation in terms of the rate of energy exchange attainable over time. In the alternative, use of supersaturated steam creates inefficiencies due to the potential need to remove excess water from the system and the less than maximal use of the total energy exchange available through condensation potential.

The presence of entrained air in steam, which would otherwise cut down on the efficiency of the energy exchange through the condensation/evaporation process, is preferably minimized such as by only using steam from well boiled water. This may be accomplished by using a reboiler. Similarly, specific chemical methods are available for the removal of impurities such as air or water from other treatment gases.

The gas supply should be connected to the device with ducting that creates minimal resistance to flow. This is particularly necessary for steam treatment in order to minimize the potential for superheating and its incumbent loss of efficiency in the energy transfer process as discussed above. Likewise, any liquid water entrained in the system is preferably removed from the steam by, for example, an impingement/centrifugal separator.

In the case of steam, control of the speed and amount of energy transfer to and from the material during the treatment cycle is essential for success. After treatment, the added heat energy must be removed as quickly as possible. This is accomplished by exposing the chamber to vacuum. This has the effect of re-evaporating substantially all of the water condensed onto the material surface during steam treatment, and cooling the material surface down to near the point at which the treatment began. In this way nearly the same amount of heat is removed from the material as had been added. Furthermore, in the absence of condensate rundown, the heat is removed from precisely the same regions to which it had been added. The result is that the material surface is uniformly heated and then cooled to nearly its original temperature within a very short period of time. The speed of this process precludes any significant component of conductive heat transfer and thus substantially shields the interior of the material from the transient heat effects of the process.

In the case of a treatment gas other than steam, wherein pasteurization effects are achieved due to chemical rather than energy transfer processes, the value of rapid application and removal from the material surface is of similar importance. In this case the limited time of exposure minimizes subsurface diffusion of the treatment gas and any potentially undesirable effects such might cause.

Typically, the energy of activation necessary to kill microorganisms through denaturation of their vital enzymes is in the range of 2–12 kcal/g-mol. This value is far lower than the energy of activation needed to cause irreversible changes in most food materials. For example, sufficient denaturation of muscle protein to give a cooked appearance typically requires about 50–100 kcal/g-mol. Thus, on average about twelve times as much energy must be absorbed by one mole of muscle protein compared to one mole of bacterial enzyme for their respective cooking and killing to be relatively complete. Further, only micrograms of microbial enzyme need to be deactivated for their killing, as contrasted to the grams of treated material (in this case meat) which would need to undergo denaturation through cooking. So, if the heating rates for the meat and microorganisms were equal, the microorganisms would die before the meat would be irreversibly cooked. For a square centimeter of surface contaminated with 100 bacteria, fifteen million times the thermal energy would be needed to cook the meat to a depth of one bacterial length as compared to what would be needed to kill the bacteria themselves.

Further accentuating this effect of selectively killing the microorganisms is the fact that the bacteria are exposed on the material surface where they are subject to the faster effects of convective heat transfer brought about by steam condensation. In contrast, the rate of subsurface heating for the material being treated is governed by the slower effects of conductive heat transfer.

Materials treatable by the instant invention are limited only by the fact that they should not undergo any undesirable physical changes of an irreversible nature. Food type materials such as meats, fruits, vegetables and fungi are all amenable to this process. Exemplary meats include fish, shellfish, poultry, pork, beef, and processed meats such as hot dogs, and sausage. Exemplary fruits include apples, peaches, pears, plums, cherries, nectarines, papaya, oranges, grapefruit, melons, cantaloupes and pineapples. Other items taxonomically classified as fruits, though not conventionally thought of as such, may likewise be treated by the processes of this invention. Such items include: 1) nuts such as pecans, walnuts, chestnuts, hickory nuts, pistachios, filberts and almonds; 2) grains such as corn, wheat, rice oats, milo and buckwheat; 3) legumes such as beans and peas as well as tomatoes and cucumbers. Exemplary vegetables that may be treated by the invention include carrots, broccoli, radishes, cauliflower, peppers, beets and potatoes. Non-food type materials that may be treated by the instant invention include clothing, surgical equipment, agricultural equipment, filter equipment, storage containers, and growth substrates.

Treatment conditions will vary depending on the materials involved and the degree of pasteurization desired.

Vacuum times will typically range from about 0.004 s to about 1.0 s, preferably from about 0.1 s to about 0.5 s. Vacuum absolute pressures will typically range from about 0.5 psia to about 7 psia, preferably from about 0.9 psia to about 1.9 psia. It is noted that these pressure values represent the resultant pressure in the treatment cavity at the end of the vacuum step. In the case of steam as the treatment gas, it is desired from a standpoint of thermal efficiency and reduced processing time that it be as close to its saturation temperature as practical, with this temperature typically ranging from about 220° F. to about 350° F. Steam times will typically range from about 0.004 s to about 1.0 s, preferably from about 0.05 s to about 0.1 s. Corresponding steam pressures will typically range from 16 psig to about 140 psig.

When using other gases as the sterilizing medium, the appropriate times, temperatures and pressures requisite for achieving the desired degree of surface sterilization would be readily determinable by the skilled artisan.

II. The Preferred Apparatus

With reference to FIGS. 3, 4, 5 and 6, one device that may be used in accord with the present invention is comprised of a central product valve 1 with one or more treatment valves 2 attached. Means are provided to rotate the product valve rotor 3 alternately aligning the product valve chamber 4 with the treatment valves 2 and the environment via product valve body openings 11 and 12. Means are provided to rotate the treatment valve rotor 5 very rapidly about its horizontal axis to precisely determined angular positions. In this description the motion of the treatment valve rotor 5 may be spoken of as intermittent. In actual practice, the treatment valve rotor 5 may turn in a steady motion. In this description the product valve rotor 3 is spherical with a cylindrical product chamber 4 bored through it perpendicular to the axis of rotation of the product valve rotor 3, though other configurations with other geometries may be used in the alternative. A screen shelf 9 at one end prevents the material sample from falling out the bottom. The shelf slides on a rail to effect closure of the bottom regardless of which end is the bottom at any given time. In actual practice the product valve rotor 3 may be longer, approximating a cylinder with several product chambers 4 bored through it perpendicular to its rotation. The product chambers may be of a cross section more closely fitting the material to be treated.

The desired cross section of the treatment chamber determines the diameter of the product valve rotor and treatment valve rotors. As an example, a chamber large enough to treat whole broiler chickens must be approximately eight inches in diameter and ten inches long. The product valve rotor 3 must be 13.5 inches in diameter and the treatment valve rotors 5 are approximately 11 inches in diameter.

A single treatment valve headplate 8 is provided with two openings to the vacuum 6 and two openings to the treating gas 7. The openings are arranged in pairs so that the forces that they impart on the treatment valve rotor cancel out. A single treatment valve rotor 5 has two openings 16 bored through its thickness that are arranged to align with the paired vacuum and treatment gas openings in the treatment valve headplate. See FIGS. 3, 4, 9, and 10. The connections to the vacuum receiver 14 and the gas generator 15 are preferably such that no parts of the connections are of smaller cross sectional area than the openings 16 in the treatment valve rotor 5 and the sum of the areas of the openings 16 in the treatment valve rotors 5 approximates the cross sectional area of the product chamber 4. For optimal energy transfer, the treatment valve rotors 5 are placed as close to the product treatment chamber 4 as possible and the connections to the sources of vacuum and treatment gas are made as short as possible. The positions of the product valve rotor 3 in terms of function are: removal/insertion (open to air), closed (chamber aligned with treatment valves) and removal/insertion again. See FIGS. 2A, 2B and 2C. The positions of the treatment valve rotor openings in terms of the function of each are: closed, vacuum, and gas treatment. See FIGS. 2D, 2E and 2F.

The treatment valve rotor 5 fits inside the headplate 8. The treatment valve headplate contains seal assemblies 10 at each vacuum and treatment gas opening to eliminate leakage across the process segments when closed. A section of a typical seal assembly 10 is shown in FIG. 5.

FIGS. 7, 8, 9, and 10 illustrate specific configuration and structural details of an embodiment of an apparatus designed in accordance with the present invention.

Figure 11:
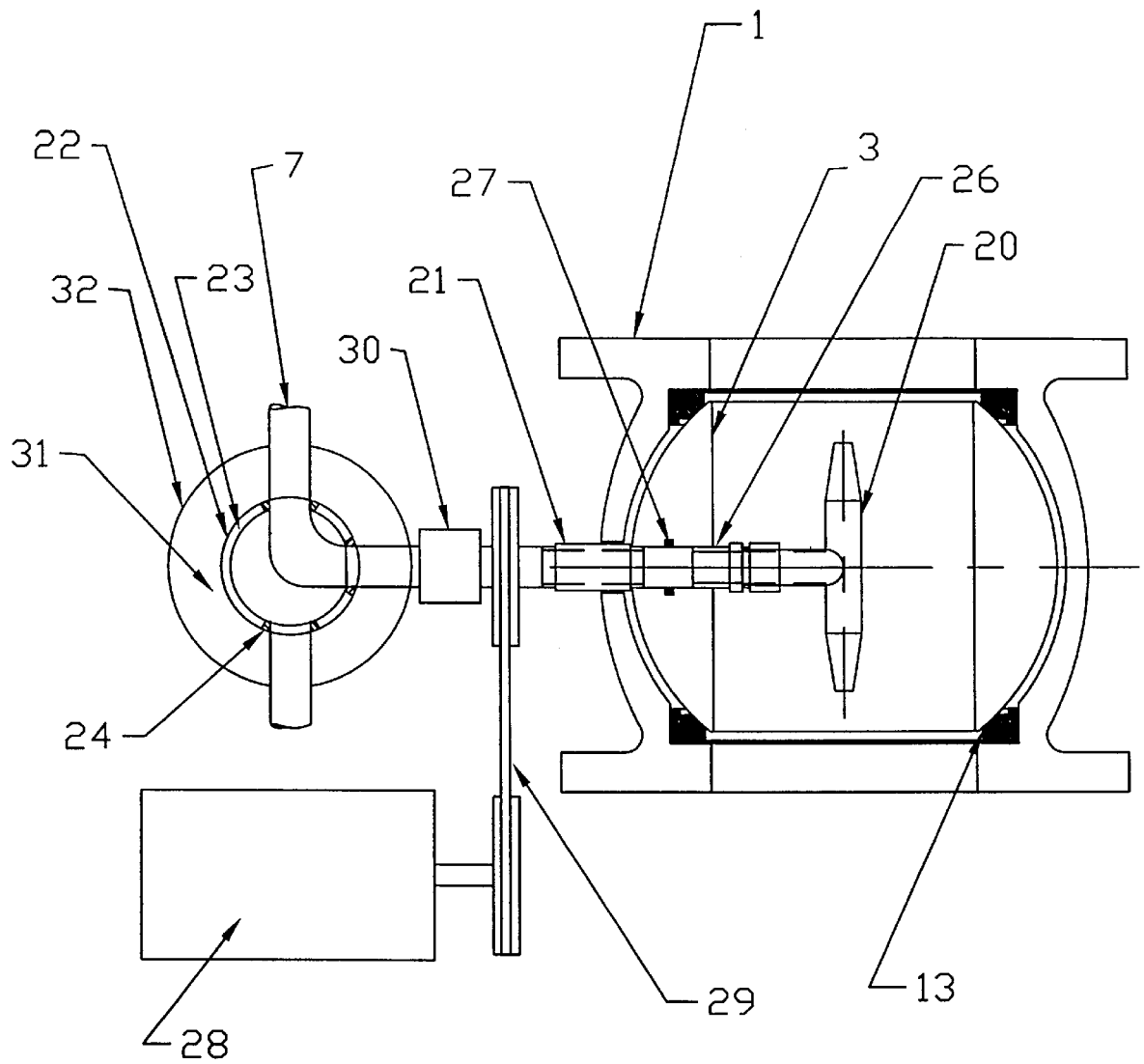
FIG. 11 is a schematic representation of a preferred embodiment of the invention wherein a gas treatment mandrel is located within the material treating apparatus product valve.

With reference to FIG. 11, a preferred embodiment of the invention that effects uniform treatment of material possessing an internal cavity, such as a chicken carcass, is comprised of a product mandrel 20 and mandrel treatment valve 31. The mandrel 20 is fabricated of any acceptable material capable of withstanding the process conditions, such as metal, glass, or plastic. The mandrel further possesses holes, slots or perforations capable of effective transfer of the air and treatment gases in and out of the cavity region of the commodity during the treatment cycle. The mandrel may be tubular or alternatively of any geometric configuration so as to closely resemble the internal shape of the commodity to be treated. It may further include spacers or standoff to maintain the position of the commodity relative to the mandrel 20 during processing and may be "T" shaped, double ended as depicted in FIG. 11 or "L" shaped single ended. The mandrel 20 is connected to hollow tube 26 which passes through product valve rotor 3 and product valve body 1 coaxial to the axis of rotation of product valve rotor 3. Tube seal 27 prevents leakage between the product valve chamber 4 and the environment via the penetration of hollow tube 26 through the product valve rotor 3. Hollow tube 26 and mandrel 20 may be locked to product valve rotor 3 to rotate with it or they may be rotated independently of the product valve rotor 3 via drive 28 and linkage 29. Rotary joint 30 connects hollow tube 26 to mandrel treatment valve 31 and allows hollow tube 26 to rotate with respect to mandrel treatment valve 31. Mandrel treatment valve 31 is comprised of mandrel treatment valve body 22, mandrel treatment valve rotor 23, seals 24, and servo 32. Mandrel treatment valve body 22 has three ports that are connected to rotary joint 30, steam source 7 and vacuum source 6. Mandrel treatment valve rotor 23 is ported to allow rotary joint 30 to be connected to steam source 7, vacuum source 6 or isolated from the environment in a closed position, mandrel treatment valve rotor 23 is connected to servo 32 which allows it to be precisely and rapidly positioned to the steam, vacuum and closed positions described. All components are designed to minimize and preclude the possibility of superheat.

III. The Preferred Process

A. Insertion

With reference to FIGS. 2A, 2B, 2D and 6, the material to be treated is first inserted into the chamber 4 through the upper body opening 11 where it rests on the screen 9. Treatment valve rotors 3 are in a position such that the openings 16 are not aligned with the openings to either the vacuum 6 or to the treatment gas 7 in the headplates 8. The treatment valves 2 are said to be in the closed position.

The product valve rotor 3 then rotates through 90 degrees aligning the product chamber 4 with the treatment control valves 2. Seals 13 isolate the treatment chamber from the environment.

B. Evacuation

Figure 2C:
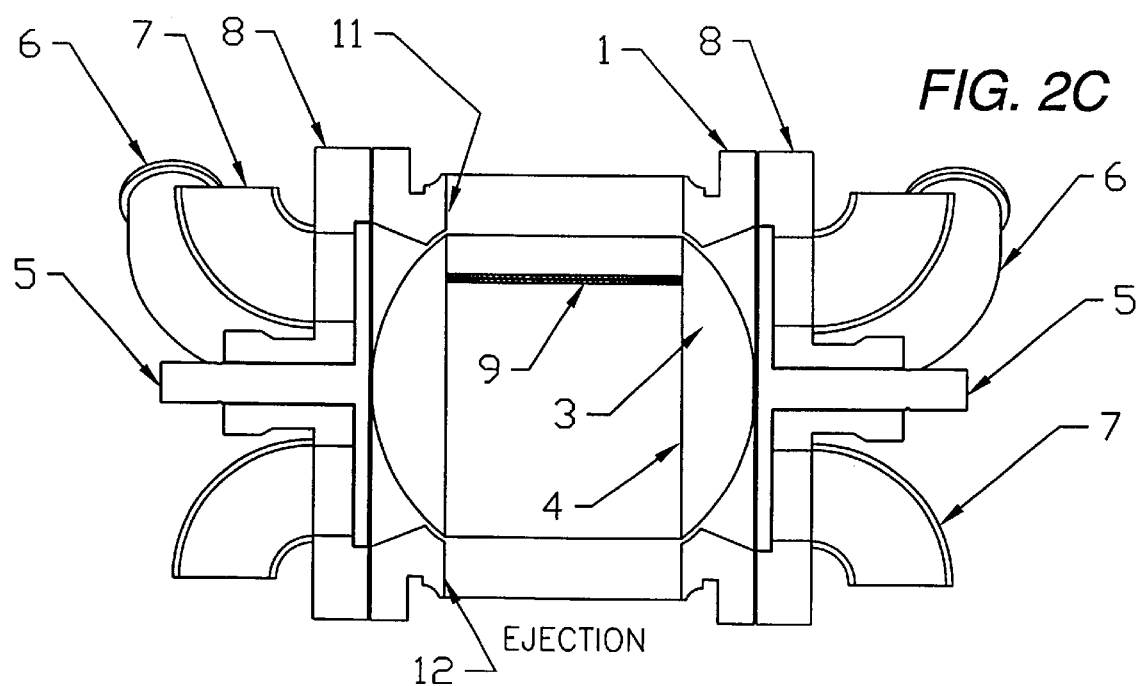
Figure 2D:
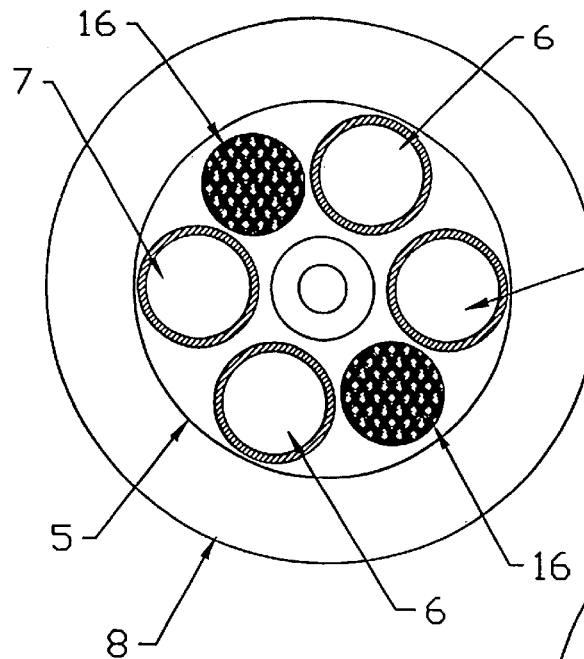
FIGS. 2D, 2E and 2F are schematic representations of a preferred material treating apparatus treatment valve at various stages throughout the material treating process.
Figure 2E:
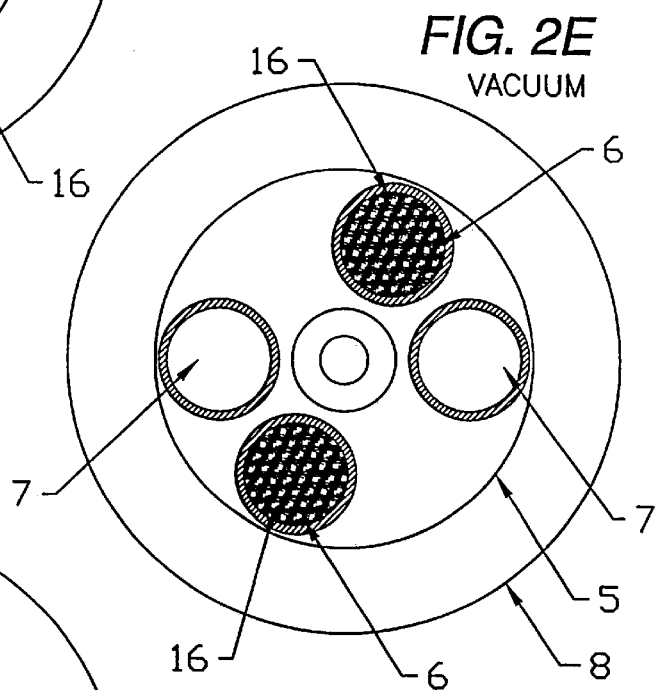

With reference to FIGS. 2D, 2E, 2F, 3, 4, 5, 6, 7, 8, 9 and 10 the treatment valve rotor 5 then rotates from the closed position to the vacuum position (FIGS. 2D and 2E). This exposes the product chamber 4 to the path leading to the vacuum receiver 14 via the rotor openings 16. The rotor 5 remains in this position long enough for the air content of the chamber to be reduced nearly to the vacuum pressure. This time can be calculated by assuming the gas flows through the stator openings at sonic velocity. Since the pressure reduction will immediately start to cool the material, the rotor 5 must stay in this position no longer than necessary. The preferred vacuum is about 0.5 psia, which is the pressure of saturated steam at 80° F.

C. Treatment

Figure 2F:
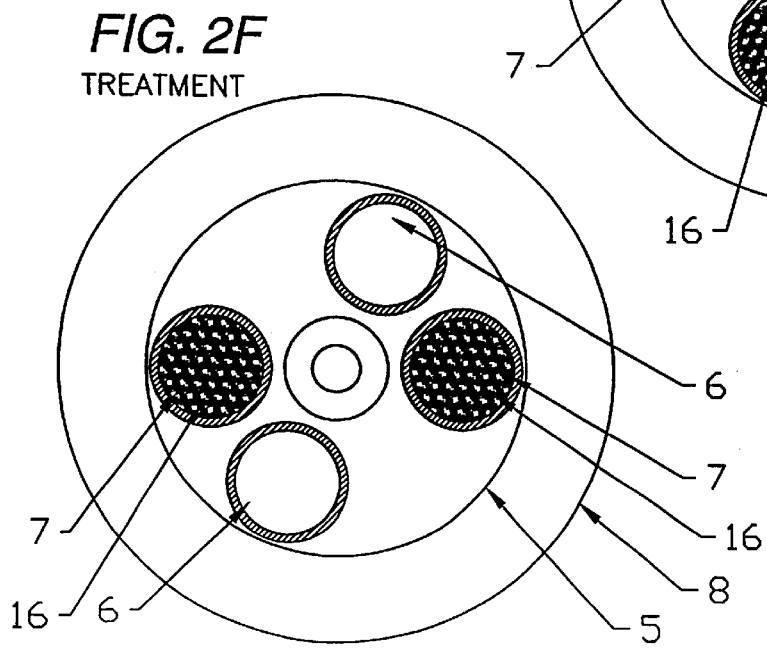

With reference to FIGS. 2E, 2F, 3, 4, 5, 6, 7, 8, 9 and 10 the treatment valve rotor 5 then rotates through an angle such that it is closed to the vacuum and open to the treatment gas reservoir, via rotor openings 16 (FIGS. 2E and 2F). In the case of steam, this is generated in the gas generator 15 by prolonged boiling of a pool of pure water within the reservoir by means of heat transferred to the pool from an energy source such as a submerged electric or steam reboiler controlled by the pool temperature. The treatment valve rotor 5 is rotated so that it passes through the closed (FIG. 2D) position in between the vacuum and the gas treatment position. This is done so that the openings in the rotor 16 do not bridge the vacuum and treatment gas openings at any time which would result in exposing the chamber to a steam vacuum flush. In an alternate embodiment of the invention the valve treatment rotor 5 is configured such that at a specific point in its rotation both treatment gas and vacuum parts are open simultaneously to effect just such a flush.

D. Cooling

With reference to FIGS. 2D, 2E, 2F, 3, 4, 5, 6, 7, 8, 9 and 10 the treatment valve rotor 5 then rotates through an angle such that the opening to the treatment gas reservoir is closed and the opening to the vacuum receiver 14 is open via rotor openings 16 (FIGS. 2E and 2F). The rotation is such that it passes through the closed (FIG. 2D) position in between the gas treatment and vacuum position. This is done so that the openings in the rotor 16 do not bridge the vacuum and gas treatment openings at any time exposing the chamber to a gas treatment-vacuum flush. This allows the gas treatment to be ended abruptly and in the case of steam allows rapid evaporative cooling to take place. For a vacuum maintained at 0.5 psia the surface cooling will proceed to nearly 80° F. at which point substantially all of the condensate added to the material in the treatment step has been removed.

E. Cycle Repetition

To maximize the efficiency of the treatment in certain situations, it may be preferable to repeat the gas treatment after the first cooling. The complete cycle of evacuation, gas treatment, and cooling may be repeated as often as necessary. If unrestrained material pieces are treated several times, it is less likely that any individual area of the material surface will escape treatment.

F. Removal

Figure 6:
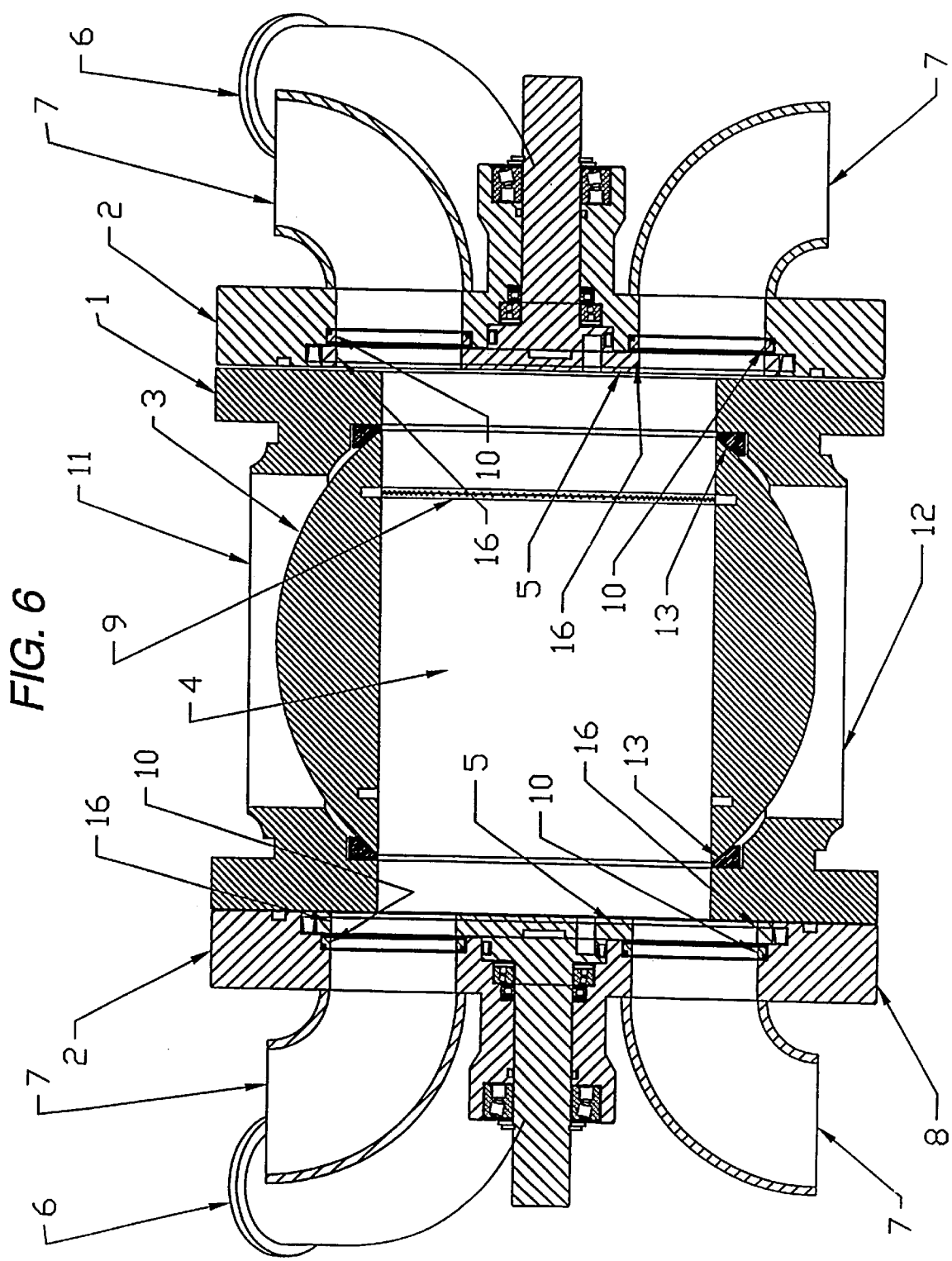
FIG. 6 is a lateral section of the product valve and treatment valves in the preferred material treating apparatus in accordance with the present invention.
Figure 7:
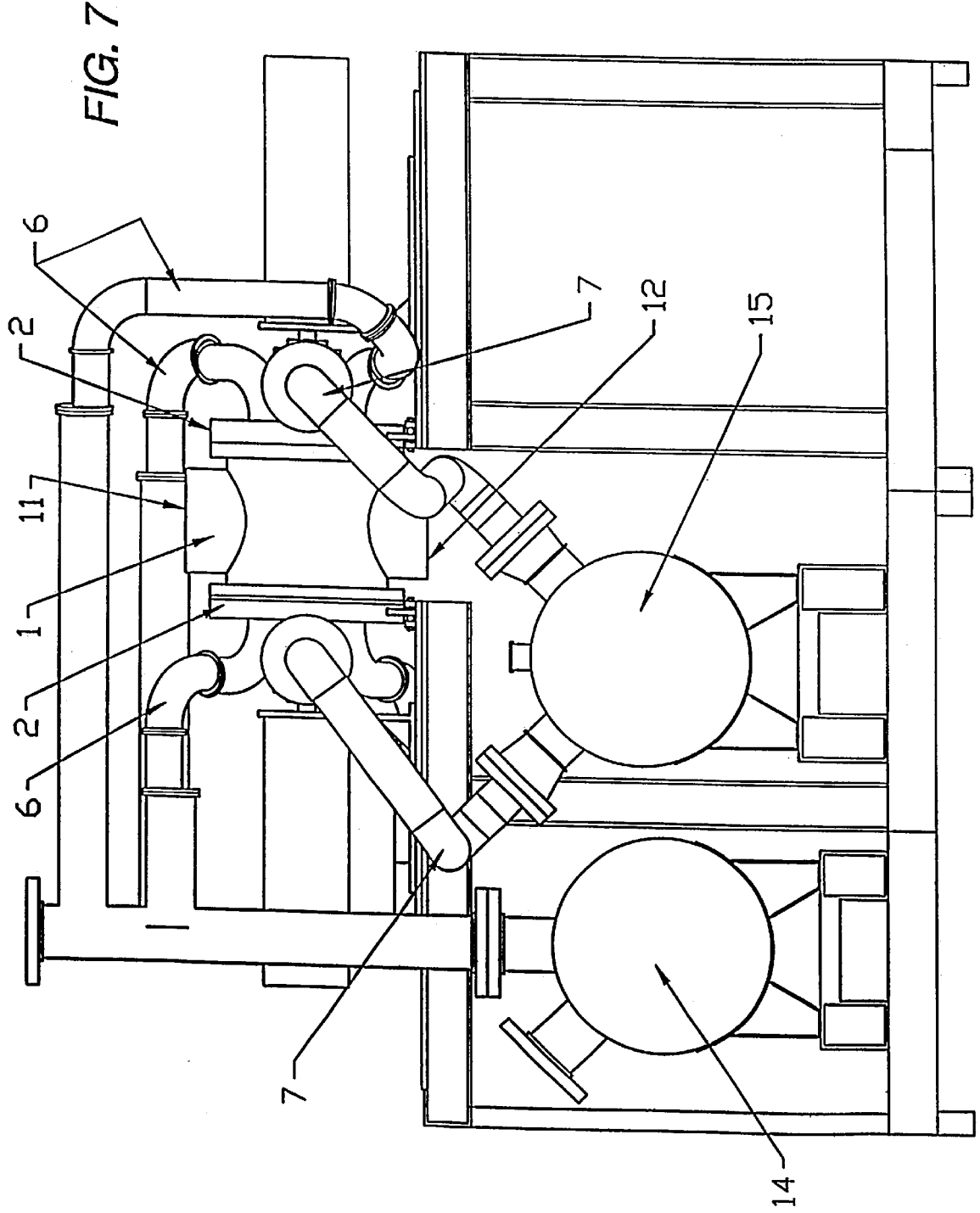
FIG. 7 is a lateral side view of an embodiment of the present invention.
Figure 8:
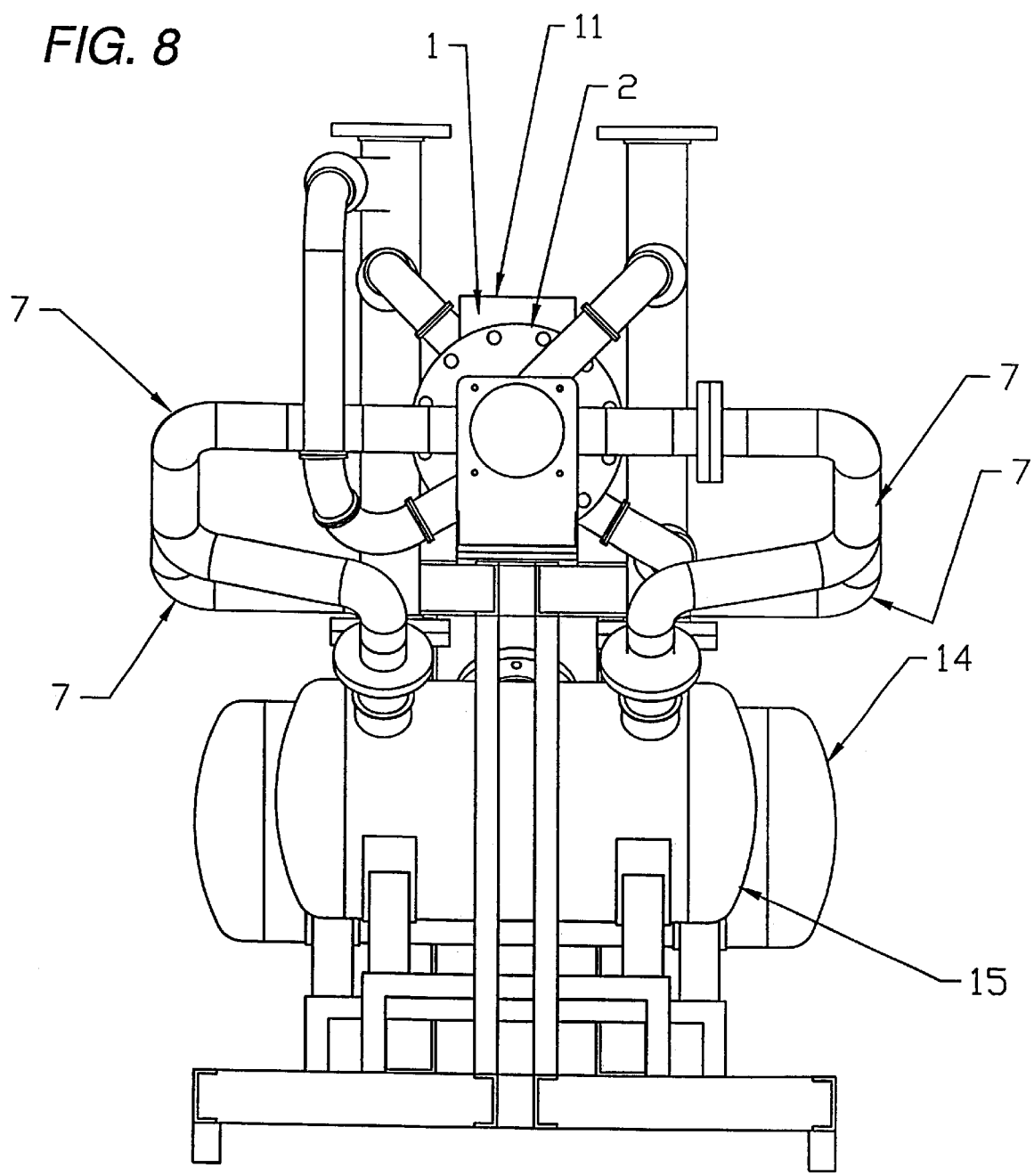
FIG. 8 is a front view of the embodiment of the present invention depicted in FIG. 7.
Figure 10:
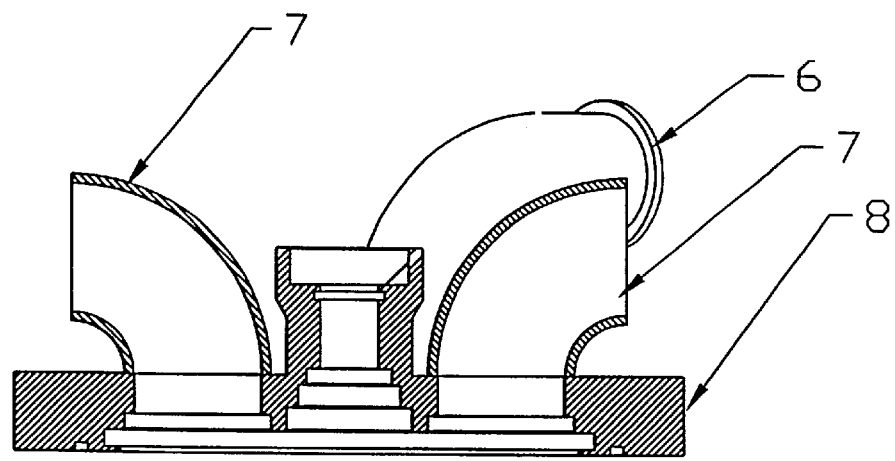
FIG. 10 is a section of the treatment valve headplate in accordance with the embodiment of the invention depicted in FIG. 7.
Figure 9:
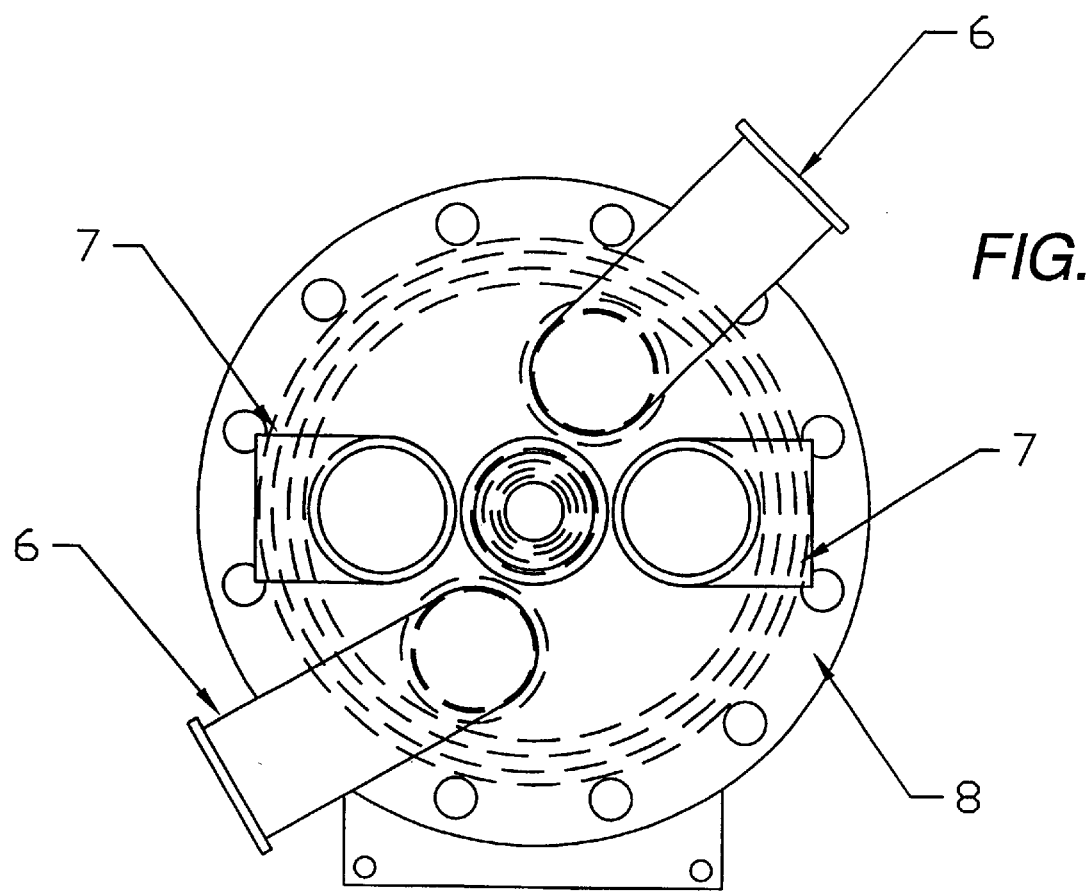
FIG. 9 is an end view of the treatment valve headplate in accordance with the embodiment of the invention depicted in FIG. 7.

At the end of the previous cycle after final vacuum and closed steps (FIGS. 2E and 2D) with reference to FIGS. 2B, 2C and 6, the product valve rotor then rotates in order o align the product chamber 4 with the environment and with the screen 9 at the current top of the product chamber. The material pieces drop through lower body opening 12 into a sanitary packaging device. The screen 9 drops to the current bottom of the product chamber and the device is ready to receive the next material pieces to be processed.

With regard to utilization of the specifically preferred embodiment of the treatment device, which includes a mandrel for the uniform treatment of materials, such as a chicken carcass, possessing an internal cavity the following analogous protocol are specifically applicable.

A. Insertion

With reference to FIGS. 2A, 2B, 2D, 6 and 11, an eviscerated carcass is first inserted into the chamber 6 through the upper body opening 11 with the visceral cavity down. It rests on mandrel 20 with the mandrel 20 inside the visceral cavity. Treatment valve rotors 5 are in a position such that the openings 16 are not aligned with the openings to either the vacuum 6 or the openings to treatment gas 7 in the headplates 8. Mandrel treatment valve rotor 23 is in a position such that the hollow tube 26 is not aligned with the openings to vacuum 6 or the openings to treatment gas 7. The treatment valves 2 and the mandrel treatment valve 31 are said to be in the closed position. The product valve rotor 3 then rotates through 90 degrees aligning the product chamber 4 with the treatment control valves 2. The mandrel 20 and hollow tube 26 may be rotated with the product valve rotor 3 aligning the eviscerated commodity backbone horizontal or may be held stationary so that the visceral cavity continues to point down. Seals 13 and 27 isolate the treatment chamber from the environment.

B. Evacuation

With reference to FIG. 11 the mandrel treatment valve rotor 23 then rotates from the closed position to the vacuum position. This exposes the product chamber 4 to the path leading to the vacuum receiver 14 via vacuum source 6, hollow tube 26 and mandrel 20. The mandrel treatment valve rotor 23 may be operated simultaneously with the treatment valve rotors 5 or may be moved slightly before the treatment valve rotors 5 to enhance the internal treatment.

C. Treatment

With reference to FIG. 11 the mandrel treatment valve rotor 20 then rotates through an angle such that it is closed to the vacuum and open to the steam reservoir 15. The mandrel treatment valve rotor 23 is moved simultaneously with the treatment valve rotors 5.

D. Cooling

With reference to FIG. 11 the treatment valve rotor 23 then rotates through an angle such that the opening to the steam reservoir 15 is closed and the opening to the vacuum receiver 14 is open. The rotation is such that it passes through the closed position in between the steam and vacuum position. This is done so that the openings in the rotor 23 do not bridge the vacuum and steam openings at any time exposing the mandrel 20 to a steam-vacuum flush. The mandrel treatment valve rotor 23 is moved simultaneously with the treatment valve rotors 5.

E. Cycle Repetition

To maximize the efficiency of the treatment in certain situations, it may be preferable to repeat the steam treatment after the first cooling. The complete cycle of evacuation, steam treatment, and cooling may be repeated as often as necessary. If unrestrained material pieces are treated several times, it is less likely that any individual area of the material surface will escape treatment.

F. Removal

At the end of the previous cycle after final vacuum and closed steps with reference to FIG. 11, the product valve rotor 3, then rotates through 90 additional degrees aligning the product chamber 4 with the environment. If the mandrel 20 was locked to rotate with the product valve rotor 3 the material pieces drop through lower body opening 12 into a sanitary packaging device. If the mandrel 20 was not rotated with the product valve rotor 3, drive 28 and linkage 29 are used to rotate the mandrel 20 180 degrees to drop the treated carcass into the sanitary packing device. If the mandrel 20 is "T" shaped the device is ready to accept the next carcass to be processed. If the mandrel 20 is "L" shaped the mandrel 20 must be rotated 180 degrees before the next carcass can be loaded.

EXAMPLE 1

Twenty-four grapefruit were treated according to the methods of the instant invention. Each combination of three parameters operating at two different conditions was tested in triplicate. Aerobic plate counts were determined for each test or control sample by shaking the sample 60 times in Butterfield solution. The sample was appropriately diluted and plated onto Tryptose Agar using a spiral plater. The plates were incubated at 37° C. for one day. Colonies were counted and expressed as log CFU/ml (colony forming units/ml). The controls or untreated samples had an average count of 3.6 log. The results for the treated samples were as follows:

| run | vacuum | steam time | steam temp | log cfu/ml | log kill |
|---|---|---|---|---|---|
| 1 | 0.25s | 0.25s | 240° F. | 3.1 | 0.5 |
| 2 | 0.75s | 0.25s | 240° F. | 2.2 | 1.4 |
| 3 | 0.25s | 0.75s | 240° F. | 1.9 | 1.7 |
| 4 | 0.75s | 0.75s | 240° F. | 0.8 | 2.8 |
| 5 | 0.25s | 0.25s | 266° F. | 0 | 3.6 |
| 6 | 0.75s | 0.25s | 266° F. | 0 | 3.6 |
| 7 | 0.25s | 0.75s | 266° F. | 0.9 | 2.7 |
| 8 | 0.75s | 0.75s | 266° F. | 0 | 3.6 |

EXAMPLE 2

Twenty-four raw unpeeled carrots were treated according to the methods of the instant invention. Each combination of three parameters operating at two different conditions was tested in triplicate. Listeria innocua was applied to 27 carrots by immersing the carrots in a solution with the bacteria. The carrots were allowed to air dry and then treated. Aerobic plate counts were determined for each test or control sample by shaking the sample 60 times in Butterfield solution. The sample was appropriately diluted and plated onto Tryptose Agar using a spiral plater. The Tryptose Agar gave the background bacteria. They were also plated onto mmVJ (modified modified Vogel Johnson) which isolates Listeria. The plates were incubated at 37° C. for one day. Colonies were counted and expressed as log CFU/ml (colony forming units/ml). The controls or untreated samples had an average count of 5.1 log. The results for the treated samples were as follows:

| run | vacuum | steam time | steam temp | log cfu/ml | log kill |
|---|---|---|---|---|---|
| 1 | 0.25s | 0.25s | 240° F. | 3.3 | 1.8 |
| 2 | 0.75s | 0.25s | 240° F. | 3.3 | 1.8 |
| 3 | 0.25s | 0.75s | 240° F. | 3.0 | 2.1 |
| 4 | 0.75s | 0.75s | 240° F. | 2.4 | 2.7 |
| 5 | 0.25s | 0.25s | 266° F. | 0 | 5.1 |
| 6 | 0.75s | 0.25s | 266° F. | 0.6 | 4.5 |
| 7 | 0.25s | 0.75s | 266° F. | 0.5 | 4.6 |
| 8 | 0.75s | 0.75s | 266° F. | 0 | 5.1 |

EXAMPLE 3

Twenty-four cantaloupe were treated according to the methods of the instant invention. Each combination of three parameters operating at two different conditions was tested in triplicate. Aerobic plate counts were determined for each test or control sample by shaking the sample 60 times in Butterfield solution. The sample was appropriately diluted and plated onto Tryptose Agar using a spiral plater. The plates were incubated at 37° C. for one day. Colonies were counted and expressed as log CFU/ml (colony forming units/ml). The controls or untreated samples had an average count of 5.6 log. The results for the treated samples were as follows:

| run | vacuum | steam time | steam temp | log cfu/ml | log kill |
|---|---|---|---|---|---|
| 1 | 0.25s | 0.25s | 260° F. | 3.1 | 2.5 |
| 2 | 0.50s | 0.25s | 260° F. | 3.2 | 2.4 |
| 3 | 0.25s | 0.75s | 260° F. | 2.1 | 3.5 |
| 4 | 0.50s | 0.75s | 260° F. | 3.0 | 2.6 |
| 5 | 0.25s | 0.25s | 280° F. | 2.2 | 3.4 |
| 6 | 0.50s | 0.25s | 280° F. | 2.3 | 3.3 |
| 7 | 0.25s | 0.75s | 280° F. | 1.6 | 4.0 |
| 8 | 0.50s | 0.75s | 280° F. | 2.6 | 3.0 |

EXAMPLE 4

Hot dogs were inoculated with Listeria innocua, 16 controls (8 inoculated and 8 not inoculated) and 40 for the test. Listeria innocua counts were determined by shaking the sample 60 times in Butterfield solution. Samples were appropriately diluted and plated onto Tryptose Agar using a spiral plater. The plates were incubated at 37° C. for one day. Colonies were counted and expressed as CFU/ml (colony forming units/ml). The non-inoculated controls had no evidence of Listeria./The inoculated controls had an average count of 124 CFU/ml. Treated samples had counts of 0 CFU/ml except for the results as listed below:

| Run | Vacuum | Steam time | Steam temp | CFU/ml |
|---|---|---|---|---|
| 1 | 0.1s | 0.1s | 280° F. | 1,1,1 |
| 2 | 0.1s | 0.3s | 280° F. | 0 |
| 3 | 0.1s | 0.5s | 280° F. | 1,1,6 |
| 4 | 0.1s | 0.2s | 280° F. | 2,2 |
| 5 | 0.1s | 0.4s | 280° F. | 2,6 |

EXAMPLE 5

Chicken samples were inoculated on the epimysial surface with 10 mL of approximately 109 cfu/ml of freshly grown *L. innocua*, SA3-VT, a nonpathogenic substitute for *L. monocytogenes*. Each drum stick was inoculated in one location. Each Cornish game hen was inoculated in three places, on the breast and on each drum stick. The culture was grown in 100 ml brain-heart infusion (Difco, Detroit) with 300 mg glucose at 28° C. for 18–24 h. The fresh culture was dripped onto the meat, which was allowed to dry inside a biological hood. Each sample was manually inserted into the treatment chamber of the surface pasteurizer. The process variables were vacuum time, steam temperature, steam time and the use or omission of a flush step. After treatment, samples were removed manually; with gloves being used for all occurrences of sample contact. After processing in the pasteurizer, samples of the inoculated areas were homogenized in a stomacher bag (Seward Medical, London) with 9.9 mL of 1 g/L peptone at room temperature. After homogenizing, dilutions in peptone were plated spirally (Spiral Systems Instruments, Cincinnati) onto Tryptose Agar (Difco, Detroit) and incubated at 37° C. After 24 hours colony forming units (cfu) were counted with a Bacteria Colony Counter, Model 500A (Spiral Systems Instruments, Cincinnati). Non-inoculated chicken samples were acquired from the processing lines, prior to immersion in the chill tank, of federally inspected processing plants. They were cooled and shipped with ice packs to prevent spoilage. Chickens, Cornish hens or broilers were cut in half from breast to neck, and pooled in a large, dry tub. Each sample was manually inserted into the treatment chamber of the surface pasteurizer. The process variables were vacuum time, steam temperature and steam time. After treatment, samples were removed manually; with gloves being used for all occurrences of sample contact. After processing in the pasteurizer, the chicken halves were placed in sterile plastic bags with 200 ml of Butterfield buffer solution and manually rinsed for 60 seconds (60 shakes). Aliquots were plated on aerobic plate count 3 M Petri film for aerobic plate count (APC) and on *E. coli* plate count 3 M Petri film for determining coliform and *E. coli*. The results from the treated samples were as follows:

Chicken Breasts

| steam time | steam temp | log kill no flush | log kill 0.05s flush |
| --- | --- | --- | --- |
| 0.1s | 138° C. | 1.4 | 1.6 |
| 0.1s | 147° C. | 2.1 | 2.1 |
| 0.1s | 150° C. | 1.7 | 2.2 |
| 0.1s | 159° C. | 2.2 | 2.0 |
| 0.1s | 160° C. | 1.6 | 2.0 |
| 0.1s | 162–163° C. | 2.3 | 1.7 |

Chicken Drumsticks

| steam time | steam temp | log kill no flush | log kill 0.05s flush |
| --- | --- | --- | --- |
| 0.1s | 138° C. | 2.2 | 2.5 |
| 0.1s | 159° C. | 3.1 | 3.2 |
| 0.1s | 160° C. | 3.1 | 3.4 |
| 0.1s | 162–163° C. | 2.5 | 2.5 |

We claim:

1. A method for subjecting a porous material to a biocidal treatment comprising the steps of:
    a. isolate the material from the environment by inserting the material into a treatment chamber;
    b. exposing the material to a first evacuation to remove a substantial amount of air from said chamber;
    c. treating the material with a substantially air-free treatment gas for a predetermined period of time sufficient to kill target organisms living on the material; and
    d. exposing the material to a second evacuation to remove a substantial amount of the air-free treatment gas;
   wherein the improvement consists of going directly from the initial vacuum step to the gas treatment step in the absence of flushing.

2. The method of claim 1 wherein the treatment gas is selected from one or more of the group consisting of steam, ozone, chlorine dioxide, hydrogen peroxide, ethylene oxide, methyl bromide, chlorine, iodine, bromine and formaldehyde.

3. The method of claim 2 wherein the treatment gas is steam.

4. The method of claim 1 wherein the pressure of the first and second evacuations does not exceed about 0.9 psia to about 1.9 psia.

5. The method of claim 1 wherein the gas treatment of the material is at a pressure ranging between about 16 psig to about 140 psig.

6. The method of claim 1 wherein the first and second evacuation steps are carried out for a time ranging from about 0.004 seconds to about 1.0 seconds.

7. The method of claim 1 wherein the gas treatment step is carried out for a time ranging from about 0.004 seconds to about 0.5 seconds.

8. The method of claim 1 wherein the steps are repeated more than once.

9. The method of claim 1 wherein the material is a food product.

10. The method of claim 9 wherein the food product is selected from the group consisting of meats, seafood, fruits, vegetables, grains and legumes.

11. The method of claim 1 wherein the material is a cavity-containing animal carcass.

12. An apparatus for subjecting a material to a biocidal treatment comprising:
    a. first vacuum means for exposing the material to a first evacuation to remove a substantial amount of air;
    b. treating means for treating the material with a substantially air-free treatment gas for a predetermined period of time sufficient to kill microorganisms living on the material; and
    c. second vacuum means for exposing the material to a second evacuation to remove a substantial amount of the air-free treatment gas;
   wherein the improvement consists of the absence of a flushing means; and wherein said apparatus further comprises a stator and a rotatable chamber, said rotatable chamber having access means; said stator having an insertion means; said first vacuum means, said treating means, said second vacuum means and said insertion means being disposed on said stator; and said rotatable chamber being intermittently rotatable inside said stator such that said access can independently contact said first vacuum means, said treating means, said second vacuum means and said insertion means.

13. The apparatus of claim 12 further comprising a mandrel located within said rotatable chamber, said mandrel being in rotatable selective communication with treatment means and vacuum means, and being capable of effective transfer of the air and treatment gases in and out of the rotatable chamber during the treatment cycle.

14. The apparatus of claim 13 wherein said mandrel is configured to resemble the internal shape of a carcass cavity.

15. The apparatus of claim 13 wherein said mandrel further possesses holes, slots or perforations.

* * * * *